United States Patent

Kamrat

[11] Patent Number: 5,606,115
[45] Date of Patent: Feb. 25, 1997

[54] MEASURES DEVICE FOR MEASURING THE RHEOLOGICAL PROPERTIES OF A SUBSTANCE

[75] Inventor: Esko Kamrat, Vantaa, Finland

[73] Assignee: Janesko, Oy, Vantaa, Finland

[21] Appl. No.: 463,034

[22] Filed: Jun. 5, 1995

[30] Foreign Application Priority Data

Feb. 27, 1995 [FI] Finland .................................. 950897

[51] Int. Cl.⁶ .................................................. G01N 11/14
[52] U.S. Cl. ......................................... 73/54.28; 73/54.35
[58] Field of Search ............................... 73/54.28, 54.29, 73/54.31, 54.35

[56] References Cited

U.S. PATENT DOCUMENTS

| 2,242,419 | 3/1941 | Cowles | 73/54.28 |
| 3,572,086 | 3/1971 | Johnston | 73/59 |
| 3,722,262 | 3/1973 | Gilinson, Jr. et al. | 73/54.28 |
| 4,468,953 | 9/1984 | Garritano | 73/60 |
| 4,559,812 | 12/1985 | Kitchen | 73/54.35 |

FOREIGN PATENT DOCUMENTS

| 0419440A3 | 3/1991 | European Pat. Off. | G01N 11/16 |
| 40754 | 5/1969 | Finland | G01N 9/00 |
| 3526522A1 | 1/1987 | Germany | G01N 11/10 |
| WO91/14168 | 9/1991 | WIPO | G01N 11/14 |

Primary Examiner—Hezron E. Williams
Assistant Examiner—Jay L. Politzer
Attorney, Agent, or Firm—Fitch, Even, Tabin & Flannery

[57] ABSTRACT

A measuring device for measuring the rheological properties of a substance, said measuring device comprising a sensor to be arranged in the process, a drive and a shaft for rotating the sensor in the process, and a measuring element for measuring the torque produced between the sensor rotating in the process and the process. To perform a reliable measurement, the sensor is a piece symmetrical with respect to the direction of rotation, the mechanical construction and the drive are symmetrical with respect to the direction of rotation, and the torque-measuring element is symmetrical in its structure in such a manner that it produces signals that are equal in their absolute value in the opposite directions of rotation of the sensor.

5 Claims, 1 Drawing Sheet

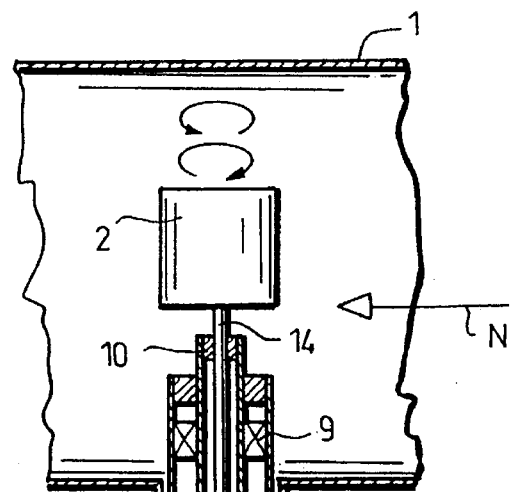
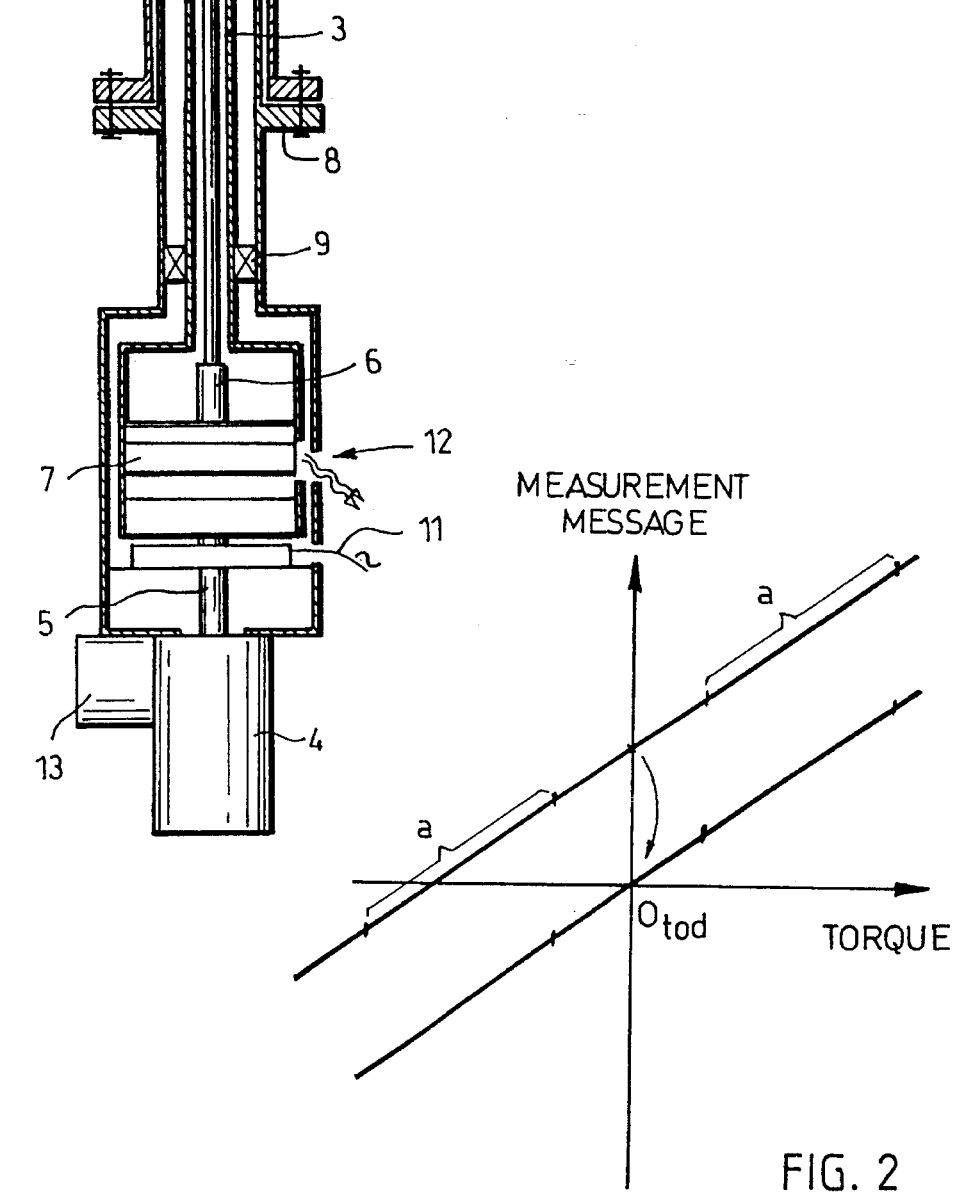
FIG. 1
FIG. 2

MEASURES DEVICE FOR MEASURING THE RHEOLOGICAL PROPERTIES OF A SUBSTANCE

BACKGROUND OF THE INVENTION

The present invention relates to a measuring device for measuring the rheological properties of a substance, said measuring device comprising a sensor to be arranged in the process, a drive and a shaft for rotating the sensor in the process, and a measuring element for measuring the torque produced between the sensor rotating in the process and the process.

Viscosity, consistency etc. can be mentioned as examples of rheological properties. It is thus necessary to perform measurements of this type in many different fields of technology. The above-mentioned measuring devices are thus largely known in many different fields. In connection with the manufacturing processes of the pulp industry, for instance, it is necessary to perform accurate measurements and to continuously control the consistency of pulp, i.e. the ratio of a solid substance such as groundwood pulp to the liquor it has sludged into. The basic principle is the measurement of the torque produced between a sensor rotating in the process and the process.

As additional examples of fields in which the above-mentioned measuring devices are used, the fields of technology relating to the processing of pulps containing cellulose and textile fibers and of different sludges can be mentioned.

As an example of the known solutions, the measuring device disclosed in Finnish Patent 40,754 can be mentioned. The technology on which the invention is based has been described in said publication.

A disadvantage of the above-mentioned known measuring device is for instance that the variations of the flow direction and speed of the pulp to be measured affect the measurement result. In addition, a problem is presented by the asymmetry of the solution, i.e. as the direction ore the flow changes, the flow does not reach one side of the slab sensor, wherefore there is no pulp flow on said side. Another disadvantage of the solution is presented by difficulties in mounting, because in practice, special connections have to used in connection with said solution. Yet another problem is caused by fouling, since the asymmetrical structure causes shadow areas to be produced, impurities thus accumulating in these areas. Correspondingly, it should be noticed that the speed of a slab sensor is lower in the middle section than in the edge area, impurities thus accumulating in the middle areas of the sensor. To arrange the cleaning of a sensor is relatively difficult to implement if the sensor is of a plate-like structure. A disadvantage is also presented by the fact that a slab sensor is subjected to great axial forces and bending forces due to the effect of the variation in the flow direction of the pulp, these forces possibly disturbing the reception of the measurement signal. Previously, problems have also been caused by phenomena which cause zero drift, i.e. hysteresis in connection with the leading of a measuring shaft caused by the process state; flow and pressure shocks caused by the process on the sensor, and shocks caused by the pieces propagating in the process on the sensor; mechanical changes caused by variations in temperature; the drift due to the aging of the measuring element; and the error torque due to the asymmetrical flow profile.

SUMMARY OF THE INVENTION

The object of the invention is to provide a measuring device by means of which the disadvantages associated with the prior art can be obviated. This is achieved with the measuring device of the invention, characterized in that the sensor is a piece symmetrical with respect to the direction of rotation, that the mechanical construction and the drive are symmetrical with respect to the direction of rotation, and that the torque-measuring element is symmetrical in its structure in such a manner that it produces signals that are equal in their absolute value in the opposite directions of rotation of the sensor.

The main advantage of the invention is that by means thereof, all the phenomena related to zero drift that are associated with the prior art can be obviated. Another advantage is presented by the fact that by changing the direction of rotation, it is possible to keep the sensor cleaner in comparison with the previously known measuring devices. Due to the symmetry of the sensor, it is possible to change the direction of rotation, all the areas of the detecting surface of the sensor thus coming into contact with the main flow in their turn, whereby said areas remain clean and the measuring properties remain constant. Yet another advantage is produced by the fact that the different strings, trims, rags and the like in the process, which can twist themselves around the sensor, can be removed by changing the direction of rotation of the sensor.

BRIEF DESCRIPTION OF THE DRAWINGS

In the following, the invention will be described in more detail by means of a preferred embodiment shown in the accompanying drawing, in which FIG. 1 shows a schematic side view of the measuring device of the invention, and FIG. 2 shows schematically the determination of the actual zero, this determination being achieved with the invention.

DESCRIPTION

FIG. 1 shows schematically a preferred embodiment of the measuring device of the invention. Reference numeral 1 is used for indicating a process pipe, i.e. a pipe in which the substance, such as pulp, included in the process flows. The main direction of flow of the substance included in the process is indicated by arrow N in FIG. 1. Reference numeral 2 indicates the sensor to be arranged in the process, and reference numeral 3 indicates the shaft by means of which the sensor 2 is rotated by means of a drive 4. The drive can be any suitable motor, such as an electric motor.

In FIG. 1, reference numeral 5 indicates the coupling means, and reference numeral 6 indicates the torque-measuring element for measuring the torque created between the sensor 2 rotating in the process and the process. Reference numeral 7 indicates the signal amplifier in FIG. 7. In FIG. 1, reference numeral 8 indicates the process connection, by means of which the measuring device is mounted on the process pipe 1. Reference numeral 9 indicates the bearings, reference numeral 14 indicates the measuring shaft transmitting the torque from the process state, and reference numeral 10 indicates the lead-in of the measuring shaft 14. Power feed to the measuring device, i.e. to the torque-measuring element 6 and the signal amplifier 7 is denoted by reference numeral 11. The power feed can be implemented by any suitable manner which is independent of the direction of rotation of the sensor. The measuring data from the above-mentioned device operated by rotation can be transmitted for instance to a suitable display unit by any suitable manner which is independent of the direction of rotation of the sensor, for instance optically, as indicated by reference numeral 12 in FIG. 1.

According to the essential idea of the invention, the sensor 2 is a piece symmetrical with respect to the direction of rotation. The mechanical construction and the drive 4 are correspondingly symmetrical with respect to the direction of rotation. The torque-measuring device 6 is also symmetrical in structure in such a manner that it produces signals that are equal in their absolute value in the opposite directions of rotation of the sensor 2.

The sensor 2 can be any piece symmetrical with respect to the direction of rotation, for instance the cylindrical piece disclosed in Finnish Patent Application 950,897 filed simultaneously with the present application. The invention is by no means, however, restricted to the above-mentioned piece, but the sensor can be for instance a plate-like piece, spherical piece or some other body of revolution.

The amplifier 7 of the signal obtained from the torque-measuring element 6 and the possible converters are arranged correspondingly to operate symmetrically with respect to the direction of rotation. The converters can be for instance any suitable converters.

By means of the construction described above, it is possible to perform measurements by rotating the sensor in either direction, because the measurement results are the same irrespective of the direction of rotation. This is also made possible by the fact that the measuring device is equipped with means 13, which are arranged to change the direction of rotation of the sensor so as to be the opposite at predetermined intervals, i.e. the sensor 2 is first rotated in one direction for a certain period of time, after which the direction of rotation is changed to be the opposite, and the rotation is continued in this direction for a predetermined period of time. Next, the direction of rotation is changed again, etc. The means 13 can be any suitable means, for instance devices based on the measurement of time, devices based on the number of revolutions, etc. The opposite directions of rotation of the sensor 2 are indicated by arrows in FIG. 1.

Due to the change of the direction of rotation, the sensor is kept clean in an effective manner, because due to the change of the direction of rotation, even the strings and similar pieces caught on the sensor 2 can be removed.

As a result of the possibility of changing the direction of rotation, it is also possible to find the actual zero of the measurement in a preferred manner. The zero varies for instance due to hysteresis, as stated above. The determination of the actual zero is shown schematically in FIG. 2.

FIG. 2 shows the interdependence of the torque and measurement message. In FIG. 2, reference symbol a is used for indicating the measurement areas in different directions of rotation. By storing the measurement message before the change of the direction of rotation and after it, the actual zero $0_{tod}$ can be determined from the data obtained in this manner by calculating. In the manner described above, it is possible to obviate the phenomena causing zero drift in the previously known solutions as stated above.

The embodiment described above is by no means intended to restrict the invention, but the invention can be modified quite freely within the scope of the claims. It is thus apparent that the measuring device of the invention or its details do not have to be exactly like presented in the figures, but also other types of solutions are possible. For instance, the bearing assembly and the lead-in do not necessarily have to be exactly like shown in the figure, but the details concerned can be implemented in any manner known as such.

I claim:

1. A measuring device for measuring the rheological properties of a substance, said measuring device comprising a sensor arranged along an axis normal to the flow direction in a process flow, a reversible drive and a shaft collocated along said axis for rotating the sensor in the process in one of a first rotational direction and a second rotational direction opposite to the first rotational direction, means for reversing the direction of the drive to rotate the sensor in opposite directions and a measuring element for measuring the torque produced between the sensor and the process flow with the sensor rotating in one of the first and second rotational directions, the sensor being axially symmetric about said axis, the drive and the mechanical connections between the drive and the sensor being axially symmetric about said axis, and the torque-measuring element producing output proportional to the absolute value of the torque in both the opposite directions of rotation of the sensor.

2. A measuring device according to claim 1, further including a signal amplifier for the torque-measuring element and a power feed for the torque-measuring element and the signal amplifier with the output of the measuring element and amplifier independent of the rotational direction of the sensor so as to be proportional to the absolute value of the torque.

3. A measuring device according to claim 1, wherein the measuring device comprises means to reverse the direction of rotation at predetermined intervals.

4. A measuring device according to claim 2, wherein the measuring device comprises means to reverse the direction of rotation at predetermined intervals.

5. A measuring device for measuring the rheological properties of a substance flowing in a flow direction in a pipe, the measuring device comprising:

a sensor mounted in the pipe in contact with the flowing substance;

a drive for rotating the sensor in the pipe about an axis of rotation normal to the flow direction;

a torque measuring element which measures the torque created between the sensor rotating in the flowing substance and the flowing substance, wherein the drive is reversible for rotating the sensor in one of a first rotational direction and a second rotational direction opposite to the first rotationed direction to clean the sensor by the substance flow for obtaining accurate measurements of the torque between the sensor and flowing substance.

* * * * *

UNITED STATES PATENT AND TRADEMARK OFFICE
CERTIFICATE OF CORRECTION

PATENT NO. : 5,606,115
DATED : February 25, 1997
INVENTOR(S) : Esko KAMRAT

It is certified that error appears in the above-indentified patent and that said Letters Patent is hereby corrected as shown below:

On the title page, item [54], and col.1, line 1 in the first line of the title, change "MEASURES DEVICE" to --MEASURING DEVICE--.

At column 4, line 53 (Claim 4) change "rotationed" to --rotational--.

Signed and Sealed this

Eighth Day of July, 1997

Attest:

BRUCE LEHMAN

Attesting Officer

Commissioner of Patents and Trademarks